(12) United States Patent
Firkins

(10) Patent No.: US 8,425,563 B2
(45) Date of Patent: Apr. 23, 2013

(54) SPINAL ROD SUPPORT KIT

(75) Inventor: Paul Firkins, Neuchatel (CH)

(73) Assignee: DePuy International Ltd., Leeds (GB)

( * ) Notice: Subject to any disclaimer, the term of this patent is extended or adjusted under 35 U.S.C. 154(b) by 452 days.

(21) Appl. No.: 11/622,251

(22) Filed: Jan. 11, 2007

(65) Prior Publication Data

US 2007/0179501 A1 Aug. 2, 2007

(30) Foreign Application Priority Data

Jan. 13, 2006 (GB) .................................. 0600662.1

(51) Int. Cl.
*A61B 17/70* (2006.01)

(52) U.S. Cl.
USPC ........................................................ 606/259

(58) Field of Classification Search .................. 606/246, 606/250–261, 278–279; 428/188
See application file for complete search history.

(56) References Cited

U.S. PATENT DOCUMENTS

| | | |
|---|---|---|
| 2,669,896 A | 2/1954 | Clough |
| 2,952,285 A | 9/1960 | Roosli |
| 3,604,487 A | 9/1971 | Gilbert |
| 3,786,806 A | 1/1974 | Johnson |
| 3,915,160 A | 10/1975 | Lode |
| 4,289,123 A | 9/1981 | Dunn |
| 4,363,250 A | 12/1982 | Suga |
| 4,592,933 A | 6/1986 | Meyerson |
| 4,611,582 A | 9/1986 | Duff |
| 4,697,582 A | 10/1987 | William |
| 4,733,657 A | 3/1988 | Kluger |
| 4,743,260 A | 5/1988 | Burton |
| 4,887,596 A | 12/1989 | Sherman |
| 4,957,495 A | 9/1990 | Kluger |
| 4,987,892 A | 1/1991 | Krag |
| 5,005,562 A | 4/1991 | Cotrel |
| 5,042,982 A | 8/1991 | Harms |
| 5,067,955 A | 11/1991 | Cotrel |
| 5,092,866 A | 3/1992 | Breard |
| 5,102,412 A | 4/1992 | Rogozinski |

(Continued)

FOREIGN PATENT DOCUMENTS

| | | |
|---|---|---|
| DE | 3923996 | 8/1993 |
| DE | 9218381 | 2/1994 |

(Continued)

OTHER PUBLICATIONS

Advanced Energy, Industrial Processes: "Infrared (IR) Heating," "Microwave Heating," Radio Frequency and "Catalytic Heating," (2003).

(Continued)

*Primary Examiner* — Eduardo C Robert
*Assistant Examiner* — Steven Cotroneo

(57) ABSTRACT

A spinal support rod kit for the treatment of spinal column shape deformations, comprises a first spinal support rod whose cross-section is non-circular at least at one end thereof and a second spinal support rod whose cross-section is circular along at least part of its length. A socket attached to the second support rod at one end is shaped so that the non-circular end of the first support rod can be received in the socket. The second support rod can include a mechanical locking component which can engage the non-circular end of the first support rod when it is inserted into the socket to prevent it from being withdrawn.

7 Claims, 4 Drawing Sheets

U.S. PATENT DOCUMENTS

| | | | |
|---|---|---|---|
| 5,120,171 A | 6/1992 | Lasner |
| 5,129,388 A | 7/1992 | Vignaud |
| 5,129,900 A | 7/1992 | Asher |
| 5,133,716 A | 7/1992 | Plaza |
| 5,176,678 A | 1/1993 | Tsou |
| 5,176,680 A | 1/1993 | Vignaud |
| 5,181,917 A | 1/1993 | Rogozinski |
| 5,190,543 A | 3/1993 | Schlapfer |
| 5,207,678 A | 5/1993 | Harms |
| 5,219,349 A | 6/1993 | Krag |
| 5,226,766 A | 7/1993 | Lasner |
| 5,263,939 A | 11/1993 | Wortrich |
| 5,282,801 A | 2/1994 | Sherman |
| 5,282,863 A | 2/1994 | Burton |
| 5,290,289 A | 3/1994 | Sanders |
| 5,312,404 A | 5/1994 | Asher |
| 5,330,473 A | 7/1994 | Howland |
| 5,360,431 A | 11/1994 | Puno |
| 5,385,565 A | 1/1995 | Ray |
| 5,387,212 A | 2/1995 | Yuan |
| 5,387,213 A | 2/1995 | Breard |
| 5,391,168 A | 2/1995 | Sanders |
| 5,413,576 A | 5/1995 | Rivard |
| 5,415,661 A | 5/1995 | Holmes |
| 5,437,669 A | 8/1995 | Yuan |
| 5,437,673 A | 8/1995 | Baust |
| 5,445,140 A | 8/1995 | Tovey |
| 5,466,238 A | 11/1995 | Lin |
| 5,468,241 A | 11/1995 | Metz Stavenhagen |
| 5,487,742 A | 1/1996 | Cotrel |
| 5,487,744 A | 1/1996 | Howland |
| 5,499,983 A | 3/1996 | Hughes |
| 5,501,684 A | 3/1996 | Schlapfer |
| 5,520,689 A | 5/1996 | Schlapfer |
| 5,536,127 A | 7/1996 | Pennig |
| 5,536,268 A | 7/1996 | Griss |
| 5,540,688 A | 7/1996 | Navas |
| 5,540,689 A | 7/1996 | Sanders |
| 5,545,165 A | 8/1996 | Biedermann |
| 5,549,552 A | 8/1996 | Peters |
| 5,549,608 A | 8/1996 | Errico |
| 5,586,983 A | 12/1996 | Sanders |
| 5,591,166 A | 1/1997 | Bernhardt |
| 5,593,407 A * | 1/1997 | Reis ........................... 606/261 |
| 5,593,408 A | 1/1997 | Gayet |
| 5,597,378 A | 1/1997 | Jervis |
| 5,601,552 A | 2/1997 | Cotrel |
| 5,626,581 A | 5/1997 | Staehlin |
| 5,630,816 A | 5/1997 | Kambin |
| 5,645,520 A | 7/1997 | Nakamura |
| 5,649,931 A | 7/1997 | Bryant |
| 5,651,789 A | 7/1997 | Cotrel |
| 5,658,286 A | 8/1997 | Sava |
| 5,667,513 A | 9/1997 | Torrie |
| 5,672,175 A | 9/1997 | Martin |
| 5,672,176 A | 9/1997 | Biedermann |
| 5,702,452 A | 12/1997 | Argenson |
| 5,725,527 A | 3/1998 | Biedermann |
| 5,738,685 A | 4/1998 | Halm |
| 5,743,907 A | 4/1998 | Asher |
| 5,743,911 A | 4/1998 | Cotrel |
| 5,766,004 A | 6/1998 | Besselink |
| 5,797,911 A | 8/1998 | Sherman |
| 5,830,179 A | 11/1998 | Mikus |
| 5,833,707 A | 11/1998 | McIntyre |
| 5,879,350 A | 3/1999 | Sherman |
| 5,882,350 A | 3/1999 | Ralph |
| 5,885,285 A | 3/1999 | Simonson |
| RE36,211 E | 5/1999 | Nonomura |
| 5,899,903 A * | 5/1999 | Cotrel ........................... 606/279 |
| 5,910,141 A | 6/1999 | Morrison |
| 5,910,142 A | 6/1999 | Tatar |
| 5,919,158 A | 7/1999 | Saperstein |
| 5,947,965 A | 9/1999 | Bryan |
| 5,947,966 A | 9/1999 | Drewry |
| 5,951,555 A | 9/1999 | Rehak |
| 5,961,515 A | 10/1999 | Taylor |
| 5,964,760 A | 10/1999 | Richelsoph |
| 5,964,770 A | 10/1999 | Flomenblit |
| 5,989,250 A | 11/1999 | Wagner |
| 5,989,254 A | 11/1999 | Katz |
| 5,997,580 A | 12/1999 | Mastrorio |
| 6,050,997 A | 4/2000 | Mullane |
| 6,063,090 A | 5/2000 | Schlapfer |
| 6,071,250 A | 6/2000 | Douglas |
| 6,074,391 A | 6/2000 | Metz Stavenhagen |
| 6,077,262 A | 6/2000 | Schlapfer |
| 6,090,110 A | 7/2000 | Metz Stavenhagen |
| 6,090,113 A | 7/2000 | Le Couedic |
| 6,102,912 A | 8/2000 | Cazin |
| 6,106,527 A | 8/2000 | Wu |
| 6,110,172 A | 8/2000 | Jackson |
| 6,127,597 A | 10/2000 | Beyar |
| 6,139,548 A | 10/2000 | Errico |
| 6,139,549 A | 10/2000 | Keller |
| 6,146,383 A | 11/2000 | Studer |
| 6,183,472 B1 | 2/2001 | Lutz |
| 6,200,317 B1 | 3/2001 | Aalsma |
| 6,204,060 B1 | 3/2001 | Mehtali |
| 6,214,006 B1 | 4/2001 | Metz Stavenhagen |
| 6,235,028 B1 | 5/2001 | Brumfield |
| 6,238,491 B1 | 5/2001 | Davidson |
| 6,241,730 B1 | 6/2001 | Alby |
| 6,254,602 B1 | 7/2001 | Justis |
| 6,261,287 B1 | 7/2001 | Metz Stavenhagen |
| 6,261,288 B1 | 7/2001 | Jackson |
| 6,267,764 B1 | 7/2001 | Elberg |
| 6,273,914 B1 * | 8/2001 | Papas ........................... 606/250 |
| 6,280,442 B1 | 8/2001 | Barker |
| 6,280,443 B1 | 8/2001 | Gu |
| 6,293,949 B1 | 9/2001 | Justis |
| 6,299,216 B1 | 10/2001 | Thompson |
| 6,302,888 B1 | 10/2001 | Mellinger |
| 6,306,141 B1 | 10/2001 | Jervis |
| 6,309,389 B1 | 10/2001 | Baccelli |
| 6,309,391 B1 | 10/2001 | Crandall |
| 6,325,805 B1 | 12/2001 | Ogilvie |
| 6,328,741 B1 * | 12/2001 | Richelsoph ........................... 606/252 |
| 6,361,637 B2 | 3/2002 | Martin |
| 6,368,321 B1 | 4/2002 | Jackson |
| 6,379,357 B1 | 4/2002 | Bernstein |
| 6,389,710 B1 | 5/2002 | Chou |
| 6,402,752 B2 | 6/2002 | Schäffler Wachter |
| 6,423,065 B2 | 7/2002 | Ferree |
| 6,440,133 B1 | 8/2002 | Beale |
| 6,440,137 B1 | 8/2002 | Horvath |
| 6,443,953 B1 | 9/2002 | Perra |
| 6,447,478 B1 | 9/2002 | Maynard |
| 6,471,716 B1 | 10/2002 | Pecukonis |
| 6,478,798 B1 | 11/2002 | Howland |
| 6,485,491 B1 | 11/2002 | Farris |
| 6,485,492 B1 | 11/2002 | Halm |
| 6,517,533 B1 | 2/2003 | Swaminathan |
| 6,520,962 B1 | 2/2003 | Taylor |
| 6,537,276 B2 | 3/2003 | Metz Stavenhagen |
| 6,540,748 B2 | 4/2003 | Lombardo |
| 6,540,749 B2 | 4/2003 | Schäfer |
| 6,551,320 B2 | 4/2003 | Lieberman |
| 6,554,834 B1 | 4/2003 | Crozet |
| 6,565,567 B1 | 5/2003 | Haider |
| 6,597,279 B1 | 7/2003 | Haraguchi |
| 6,616,669 B2 | 9/2003 | Ogilvie |
| 6,623,485 B2 | 9/2003 | Doubler |
| 6,648,888 B1 | 11/2003 | Shluzas |
| 6,652,526 B1 | 11/2003 | Arafiles |
| 6,660,006 B2 | 12/2003 | Markworth |
| 6,689,137 B2 | 2/2004 | Reed |
| 6,692,500 B2 | 2/2004 | Reed |
| 6,695,843 B2 | 2/2004 | Biedermann |
| 6,706,044 B2 | 3/2004 | Kuslich |
| 6,716,214 B1 | 4/2004 | Jackson |
| 6,730,087 B1 | 5/2004 | Butsch |
| 6,733,502 B2 | 5/2004 | Altarac |
| 6,733,531 B1 | 5/2004 | Trieu |
| 6,743,231 B1 | 6/2004 | Gray |
| 6,749,613 B1 | 6/2004 | Conchy |
| 6,755,829 B1 | 6/2004 | Bono |

| | | | | | |
|---|---|---|---|---|---|
| 6,761,719 B2 | 7/2004 | Justis | 2002/0173789 A1 | 11/2002 | Howland |
| 6,783,527 B2 | 8/2004 | Drewry | 2003/0004512 A1 | 1/2003 | Farris |
| 6,786,984 B1 | 9/2004 | Hanada | 2003/0023240 A1 | 1/2003 | Amrein |
| 6,800,078 B2 | 10/2004 | Reed | 2003/0073995 A1 | 4/2003 | Reed |
| 6,800,079 B2 | 10/2004 | Reed | 2003/0083657 A1 | 5/2003 | Drewry |
| 6,800,778 B1 | 10/2004 | Aoki | 2003/0088248 A1 | 5/2003 | Reed |
| 6,802,844 B2 * | 10/2004 | Ferree ................. 606/258 | 2003/0100896 A1 | 5/2003 | Biedermann |
| 6,837,889 B2 | 1/2005 | Shluzas | 2003/0105460 A1 | 6/2003 | Crandall |
| 6,872,208 B1 | 3/2005 | McBride | 2003/0109880 A1 | 6/2003 | Shirado |
| 6,881,220 B2 | 4/2005 | Edwin | 2003/0114853 A1 | 6/2003 | Burgess |
| 6,887,241 B1 | 5/2005 | McBride | 2003/0171749 A1 | 9/2003 | Le Couedic |
| 6,964,666 B2 | 11/2005 | Jackson | 2003/0176861 A1 | 9/2003 | Reed |
| 6,984,242 B2 | 1/2006 | Campbell | 2003/0191470 A1 | 10/2003 | Ritland |
| 6,986,771 B2 | 1/2006 | Paul | 2003/0203488 A1 | 10/2003 | Mehtali |
| 6,989,011 B2 | 1/2006 | Paul | 2003/0220642 A1 | 11/2003 | Freudiger |
| 7,010,866 B1 | 3/2006 | Lin | 2003/0220643 A1 | 11/2003 | Ferree |
| 7,044,966 B2 | 5/2006 | Svanidze | 2004/0002708 A1 | 1/2004 | Ritland |
| 7,044,982 B2 | 5/2006 | Milbocker | 2004/0049189 A1 | 3/2004 | Le Couedic |
| 7,063,706 B2 | 6/2006 | Wittenstein | 2004/0049190 A1 | 3/2004 | Biedermann |
| 7,066,938 B2 * | 6/2006 | Slivka et al. ................. 606/914 | 2004/0073215 A1 | 4/2004 | Carli |
| 7,094,237 B2 | 8/2006 | Gradel | 2004/0106921 A1 | 6/2004 | Cheung |
| 7,104,993 B2 | 9/2006 | Baynham | 2004/0158258 A1 | 8/2004 | Bonati |
| 7,125,410 B2 | 10/2006 | Freudiger | 2004/0162558 A1 | 8/2004 | Hegde |
| 7,128,743 B2 | 10/2006 | Metz Stavenhagen | 2004/0172020 A1 | 9/2004 | Beaurain |
| 7,128,758 B2 | 10/2006 | Cox | 2004/0172025 A1 | 9/2004 | Drewry |
| 7,179,261 B2 | 2/2007 | Sicvol | 2004/0181224 A1 | 9/2004 | Biedermann |
| 7,207,986 B2 | 4/2007 | Abboud | 2004/0186472 A1 | 9/2004 | Lewis |
| 7,267,687 B2 | 9/2007 | McGuckin, Jr. | 2004/0186473 A1 | 9/2004 | Cournoyer |
| 7,322,979 B2 | 1/2008 | Crandall | 2004/0204711 A1 | 10/2004 | Jackson |
| 7,335,200 B2 | 2/2008 | Carli | 2004/0215191 A1 | 10/2004 | Kitchen |
| 7,377,923 B2 | 5/2008 | Purcell | 2004/0225289 A1 | 11/2004 | Biedermann |
| 7,381,625 B2 | 6/2008 | Xi | 2004/0236330 A1 | 11/2004 | Purcell |
| 7,429,042 B2 | 9/2008 | Ban et al. | 2004/0254577 A1 | 12/2004 | Delecrin |
| 7,442,192 B2 | 10/2008 | Knowlton | 2004/0260285 A1 | 12/2004 | Steib |
| 7,455,685 B2 | 11/2008 | Justis | 2004/0267260 A1 | 12/2004 | Mack |
| 7,459,042 B2 | 12/2008 | Parker | 2004/0267275 A1 | 12/2004 | Cournoyer |
| 7,465,306 B2 | 12/2008 | Pond, Jr. | 2005/0010216 A1 | 1/2005 | Gradel |
| 7,473,267 B2 | 1/2009 | Nguyen | 2005/0010233 A1 | 1/2005 | Wittenstein |
| 7,481,827 B2 * | 1/2009 | Ryan et al. .................... 606/250 | 2005/0010778 A1 | 1/2005 | Walmsley |
| 7,491,218 B2 | 2/2009 | Landry | 2005/0033291 A1 | 2/2005 | Ebara |
| 7,494,488 B2 | 2/2009 | Weber | 2005/0033295 A1 | 2/2005 | Wisnewski |
| 7,507,248 B2 | 3/2009 | Beaurain | 2005/0038430 A1 | 2/2005 | McKinley |
| 7,559,942 B2 | 7/2009 | Paul | 2005/0065514 A1 | 3/2005 | Studer |
| 7,588,575 B2 | 9/2009 | Colleran | 2005/0065515 A1 | 3/2005 | Jahng |
| 7,604,653 B2 | 10/2009 | Kitchen | 2005/0065516 A1 | 3/2005 | Jahng |
| 7,621,912 B2 | 11/2009 | Harms | 2005/0070899 A1 | 3/2005 | Doubler |
| 7,632,292 B2 | 12/2009 | Sengupta | 2005/0070917 A1 | 3/2005 | Justis |
| 7,635,380 B2 | 12/2009 | Zucherman | 2005/0085815 A1 | 4/2005 | Harms |
| 7,641,673 B2 | 1/2010 | Le Couedic | 2005/0107788 A1 | 5/2005 | Beaurain |
| 7,658,739 B2 | 2/2010 | Shluzas | 2005/0124991 A1 | 6/2005 | Jahng |
| 7,666,189 B2 | 2/2010 | Gerber | 2005/0131408 A1 | 6/2005 | Sicvol |
| 7,691,145 B2 | 4/2010 | Reiley | 2005/0131422 A1 | 6/2005 | Anderson |
| 7,699,872 B2 | 4/2010 | Farris | 2005/0149020 A1 | 7/2005 | Jahng |
| 7,749,258 B2 | 7/2010 | Biedermann | 2005/0154390 A1 | 7/2005 | Biedermann |
| 7,763,048 B2 | 7/2010 | Fortin | 2005/0159650 A1 | 7/2005 | Raymond |
| 7,763,049 B2 | 7/2010 | Roychowdhury | 2005/0171538 A1 | 8/2005 | Sgier |
| 7,766,944 B2 | 8/2010 | Metz-Stavenhagen | 2005/0177157 A1 | 8/2005 | Jahng |
| 7,776,071 B2 | 8/2010 | Fortin | 2005/0192573 A1 | 9/2005 | Abdelgany |
| 7,780,706 B2 | 8/2010 | Marino | 2005/0192589 A1 | 9/2005 | Raymond |
| 7,789,897 B2 | 9/2010 | Sanders | 2005/0203511 A1 | 9/2005 | Wilson-MacDonald |
| 7,794,476 B2 | 9/2010 | Wisnewski | 2005/0203518 A1 | 9/2005 | Biedermann |
| 7,927,353 B2 | 4/2011 | Taylor | 2005/0222570 A1 | 10/2005 | Jackson |
| 7,976,568 B2 | 7/2011 | Cheung | 2005/0222683 A1 | 10/2005 | Berry |
| 7,988,713 B2 | 8/2011 | Metz Stavenhagen | 2005/0228376 A1 | 10/2005 | Boomer |
| 8,002,806 B2 | 8/2011 | Justis | 2005/0228378 A1 | 10/2005 | Kalfas |
| 8,007,520 B2 | 8/2011 | Metz Stavenhagen | 2005/0228379 A1 | 10/2005 | Jackson |
| 8,021,389 B2 | 9/2011 | Molz, IV | 2005/0240265 A1 | 10/2005 | Kuiper |
| 8,048,127 B2 | 11/2011 | Moulin | 2005/0245928 A1 | 11/2005 | Colleran |
| 8,048,133 B2 | 11/2011 | Biedermann | 2005/0261687 A1 | 11/2005 | Garamszegi |
| 8,075,591 B2 | 12/2011 | Ludwig | 2005/0261770 A1 | 11/2005 | Kuiper |
| 2001/0020169 A1 | 9/2001 | Metz Stavenhagen | 2005/0277932 A1 * | 12/2005 | Farris ............................ 606/61 |
| 2002/0032442 A1 * | 3/2002 | Altarac et al. .................. 606/61 | 2005/0283244 A1 | 12/2005 | Gordon |
| 2002/0035366 A1 | 3/2002 | Walder | 2005/0288668 A1 | 12/2005 | Brinkhaus |
| 2002/0082599 A1 | 6/2002 | Crandall | 2006/0009767 A1 | 1/2006 | Kiester |
| 2002/0133155 A1 | 9/2002 | Ferree | 2006/0015527 A1 | 1/2006 | Dingle |
| 2002/0138077 A1 * | 9/2002 | Ferree ............................ 606/61 | 2006/0025769 A1 | 2/2006 | Dick |
| 2002/0143327 A1 | 10/2002 | Shluzas | 2006/0036255 A1 | 2/2006 | Pond |
| 2002/0143341 A1 | 10/2002 | Biedermann | 2006/0064090 A1 | 3/2006 | Park |
| 2002/0169449 A1 | 11/2002 | Kuslich | 2006/0111715 A1 | 5/2006 | Jackson |

| | | |
|---|---|---|
| 2006/0149228 A1 | 7/2006 | Schlapfer |
| 2006/0149236 A1 | 7/2006 | Barry |
| 2006/0149237 A1 | 7/2006 | Markworth |
| 2006/0149240 A1 | 7/2006 | Jackson |
| 2006/0155277 A1 | 7/2006 | Metz Stavenhagen |
| 2006/0161152 A1 | 7/2006 | Ensign |
| 2006/0173454 A1 | 8/2006 | Spitler |
| 2006/0184171 A1 | 8/2006 | Biedermann |
| 2006/0195092 A1 | 8/2006 | Barry |
| 2006/0200129 A1 | 9/2006 | Denti |
| 2006/0200131 A1 | 9/2006 | Chao |
| 2006/0200132 A1 | 9/2006 | Chao |
| 2006/0206114 A1 | 9/2006 | Ensign |
| 2006/0217735 A1 | 9/2006 | MacDonald |
| 2006/0229607 A1 | 10/2006 | Brumfield |
| 2006/0229614 A1 | 10/2006 | Foley |
| 2006/0229615 A1 | 10/2006 | Abdou |
| 2006/0235389 A1 | 10/2006 | Albert |
| 2006/0240533 A1 | 10/2006 | Sengupta |
| 2006/0264935 A1 | 11/2006 | White |
| 2006/0264937 A1 | 11/2006 | White |
| 2006/0271193 A1 | 11/2006 | Hartmann |
| 2006/0282073 A1 | 12/2006 | Simanovsky |
| 2007/0016201 A1 | 1/2007 | Freudiger |
| 2007/0049937 A1 | 3/2007 | Matthis |
| 2007/0055240 A1 | 3/2007 | Matthis |
| 2007/0090238 A1 | 4/2007 | Justis |
| 2007/0161990 A1 | 7/2007 | Hillyard |
| 2007/0161994 A1 | 7/2007 | Lowery |
| 2007/0162007 A1 | 7/2007 | Shoham |
| 2007/0162009 A1 | 7/2007 | Chao |
| 2007/0162010 A1 | 7/2007 | Chao |
| 2007/0173800 A1 | 7/2007 | Sanders |
| 2007/0173828 A1 | 7/2007 | Firkins |
| 2007/0179501 A1 | 8/2007 | Firkins |
| 2007/0191831 A1 | 8/2007 | Sanders |
| 2007/0191841 A1 | 8/2007 | Justis |
| 2007/0191842 A1 | 8/2007 | Molz |
| 2007/0198088 A1 | 8/2007 | Biedermann |
| 2007/0213721 A1 | 9/2007 | Markworth |
| 2007/0213723 A1 | 9/2007 | Markworth |
| 2007/0239154 A1 | 10/2007 | Shaolian |
| 2007/0270843 A1 | 11/2007 | Matthis |
| 2007/0288013 A1 | 12/2007 | Sanders |
| 2008/0021456 A1 | 1/2008 | Gupta |
| 2008/0027436 A1 | 1/2008 | Cournoyer |
| 2008/0058805 A1 | 3/2008 | Stuart |
| 2008/0071373 A1 | 3/2008 | Molz |
| 2008/0114404 A1 | 5/2008 | Matthis |
| 2008/0195159 A1 | 8/2008 | Kloss |
| 2008/0234756 A1 | 9/2008 | Sutcliffe |
| 2008/0243189 A1 | 10/2008 | Purcell |
| 2008/0269805 A1 | 10/2008 | Dekutoski |
| 2009/0048632 A1 | 2/2009 | Firkins |
| 2009/0182381 A1 | 7/2009 | Beaurain |
| 2009/0198280 A1 | 8/2009 | Spratt |
| 2009/0222042 A1 | 9/2009 | Firkins |
| 2010/0010547 A1 | 1/2010 | Beaurain |
| 2010/0042156 A1 | 2/2010 | Harms |
| 2010/0063548 A1 | 3/2010 | Wang |
| 2010/0114169 A1 | 5/2010 | Le Couedic |
| 2010/0114173 A1 | 5/2010 | Le Couedic |
| 2010/0249848 A1 | 9/2010 | Wisnewski |

FOREIGN PATENT DOCUMENTS

| | | |
|---|---|---|
| DE | 9402695 | 4/1994 |
| DE | 9314297 | 5/1994 |
| DE | 4107480 | 9/1994 |
| DE | 4330837 | 3/1995 |
| DE | 10005385 | 8/2001 |
| DE | 10005386 | 8/2001 |
| DE | 20207851 | 11/2002 |
| DE | 102004010844 | 10/2005 |
| EP | 134622 | 10/1986 |
| EP | 140790 | 3/1989 |
| EP | 0470660 | 2/1991 |
| EP | 330881 | 10/1991 |
| EP | 441729 | 1/1994 |
| EP | 592266 | 4/1994 |
| EP | 328883 | 7/1994 |
| EP | 487895 | 1/1995 |
| EP | 446092 | 7/1995 |
| EP | 470660 | 7/1995 |
| EP | 572790 | 2/1996 |
| EP | 558883 | 7/1997 |
| EP | 811357 | 12/1997 |
| EP | 846444 | 6/1998 |
| EP | 564046 | 7/1998 |
| EP | 669109 | 5/1999 |
| EP | 381588 | 5/2000 |
| EP | 784693 | 10/2001 |
| EP | 1295566 | 3/2003 |
| EP | 951246 | 5/2003 |
| EP | 880344 | 8/2003 |
| EP | 1090595 | 12/2003 |
| EP | 1023873 | 10/2004 |
| EP | 885598 | 4/2005 |
| EP | 1364622 | 7/2005 |
| EP | 879579 | 8/2005 |
| EP | 1774919 | 8/2008 |
| EP | 1539005 | 6/2009 |
| EP | 1937168 | 2/2010 |
| FR | 2624720 | 6/1989 |
| FR | 2759894 | 8/1998 |
| FR | 2763831 | 12/1998 |
| FR | 2786088 | 5/2000 |
| FR | 2806615 | 9/2001 |
| FR | 2813782 | 3/2002 |
| FR | 2839880 | 11/2003 |
| GB | 412320 | 9/2005 |
| WO | 9002527 | 3/1990 |
| WO | 9822033 | 5/1998 |
| WO | 9825534 | 6/1998 |
| WO | WO 9900065 | 1/1999 |
| WO | 9944527 | 9/1999 |
| WO | 0145576 | 6/2001 |
| WO | WO 0157801 | 12/2001 |
| WO | WO 0191656 | 12/2001 |
| WO | 0207622 | 1/2002 |
| WO | 0234310 | 5/2002 |
| WO | WO 0234310 | 5/2002 |
| WO | 02102259 | 12/2002 |
| WO | 03007828 | 1/2003 |
| WO | 03049629 | 6/2003 |
| WO | 03032863 | 12/2003 |
| WO | 2004034916 | 4/2004 |
| WO | WO 2004041100 | 5/2004 |
| WO | 2004019755 | 7/2004 |
| WO | 2004103194 | 12/2004 |
| WO | WO 2004103194 | 12/2004 |
| WO | 2005030065 | 4/2005 |
| WO | 2005044123 | 5/2005 |
| WO | 2005044117 | 8/2005 |
| WO | 2006101898 | 9/2006 |
| WO | 2006084443 | 11/2006 |
| WO | WO 2006130179 | 12/2006 |
| WO | 2007041265 | 4/2007 |
| WO | 2007045892 | 4/2007 |
| WO | WO 2007045899 | 4/2007 |
| WO | WO 2008000944 | 5/2008 |

OTHER PUBLICATIONS

Andreasen G (1980) A clinical trial of alignment of teeth using 0.019-inch thermal nitinol wire with transitional temperature range between 31°C and 45°C. Am) Orthod 78:528-537.

Asher MA, Burton DC. Adolescent idiopathic scoliosis: natural history and long term treatment effects. Scoliosis 2006; 1:2.

Betz RR, Kim J, D'Andrea LP, et al. An innovative technique of vertebral body stapling for the treatment of patients with adolescent idiopathic scoliosis: a feasibility, safety, and utility study. Spine 2003;28(suppl):255-65.

Bischoff R, Bennett JT, Stuecker R, et al. The use of TexasScottish-Rite instrumentation in idiopathic scoliosis. A preliminary report. Spine 1993 18:2452-2456.

Boos N, Webb JK. Pedicle screw fixation in spinal disorders : a European view. Eur Spine) 1997;6:2-18.

Braun et al., "Mechanical modulation of vertebral growth in the fusion less treatment of progressive scoliosis in an experimental model"; Spine; May 20, 2006; 31(12):1314-20.
Braun JT, Hines JL, Akyuz E Relative versus absolute modulation of growth in the fusionless treatment of experimental scoliosis. Spine 2006, 15;31:1776-82.
Braun JT, Ogilvie JW, Akyuz E, et al. Fusionless scoliosis correction using a shape memory alloy staple in the anterior thoracic spine of the immature goat. Spine 2004;29: 1980-9.
Bridwell KH. Surgical treatment of idiopathic adolescent scoliosis. Spine 1999;24:2607-16.
Brymill Cryogenic Systems, "CRY-AC & CRY-AC-3," retrieved online at: http://www.brymill.com/catalog_1_cryac.htm (2010).
Chemtronics, Technical Data Sheet, "Freez-It Freeze Spray," TDS#1550E.
Cotrel Y, Dubousset, Guillaumat M. New universal instrumentation in spinal surgery. Clin Orthop 1988;227: 10-23.
Cryosurgery, Inc, "Verruca-Freeze is a convenient and effective cryosurgical system for the treatment of benign skin lesions," retrieved online at: http://www.cryosurgeryinc.com/cryo/cryosurgeryweb.nsf/0/9C997EB18781696E85256DCB005627D2?opendocument (2005).
Cryosurgery, Inc., "Comparison of Cryosurgical Systems,".
GHS Medical, "Our Light Coagulator Product Family," retrieved online at: http://www/ghs-medical.com/geraeteha02. htm (2005).
Gosh K, Boachie-Adjei 0, Moore C, Nishiyama M. Thoracic scoliosis fusion in adolescent and adult idiopathic scoliosis using posterior translational corrective techniques (Isola): is maximum correction of the thoracic curve detrimental to the unfused lumbar curve? Spine J 2004; 4:192-201.
Halm HF, Niemeyer T, Link TM, et al. Segmental pedicle screw instrumentation in idiopathic thoracolumbar and lumbar scoliosis. Eur Spine) 2000; 9:192-7.
Hamill CI, Lenke IG, Bridwell KH, et al. The use of pedicle screw fixation to improve correction in the lumbar s'pine of patients with idiopathic scoliosis. Is it warranted? Spine 1996;21: 1241-9.
Harrington PRo Treatment of scoliosis: correction and internal fixation by spine instrumentation. J Bone Joint Surg Am 1962;44:591-634.
Kim YJ, Lenke LG, Kim J, et al. Comparative analysis of pedicle screw versus hybrid instrumentation in posterior spinal fusion of adolescent idiopathic scoliosis. Spine 2006;31:291-298.
Lehman RA Jr, Polly DW Jr, Kuklo TR, et al. Straight-forward versus anatomic trajectory technique of thoracic pedicle screw fixation: a biomechanical analysis. Spine 2003; 28:2058-2065.
Liljenqvist UR, Halm HF, Link TM. Pedicle screw instrumentation of the thoracic spine in idiopathic scoliosis. Spine 1997;22:2239-45.
Liu XM, Wu SI, Chan YL, et al. Surface characteristics, biocompatibility, and mechanical properties of nickel-titanium plasma-implanted with nitrogen at different implantation voltages.J Biomed Mater Res A. 2007; 82:469-78.
LUMATEC "Infrared-Coagulator".
Matsumoto K, Tajima N, Kuwahara S. Correction of scoliosis with shape-memory alloy.Nippon Seikeigeka Gakkai Zasshi. Apr. 1993;67(4): 267-74.
Misenhimer GR, Peek RD, Wiltse LL, et al. Anatomic analysis of pedicle cortical and cancellous diameter as related to screw size. Spine 1989;14:367-72.
NDC, Nitinol Devices & Components, "Nitinol Technology," retrieved online at: http://www.nitinol.com/3tech.htm (2001).
Niti Smart Sheet, retrieved online at: http://www.sma.inc.com (2001).
Puttlitz et al,. A biomechanical assessment of thoracic spine stapling. Spine. Apr. 2007.
Sanders, "Preliminary investigation of shape memory alloys in the surgical correction of Scoliosis"; Spine; Sep. 15, 1993; 18(12):1640-6.
Steinmann JC, Herkowitz HN, el-Kommos H, et al. Spinal pedicle fixation: Confirmation of an image-based technique for screw placement. Spine 1993; 18:8560-61.
Suk SI, Kim W), Iee SM, Kim )H, Chung ER. Thoracic pedicle screw fixation in spinal deformities: are they really safe? Spine 2001;26:2049-57.
Suk SI, Iee CK, Kim W), et al. Segmental pedicle screw fixation in the treatment of thoracic idiopathic scoliosis. Spine 1995;20: 1399-405.
Svetlana A., Shabaloskay A. Surface corrosion and biocompatibility aspects of Nitinol as an implant material, Journal of Biomedical Materials Engineering, 2002, 12: 692109.
Szold A, Nitinol: shape-memory and super-elastic materials in surgery. Surg Endosc. 2006;20:1493-1496. doi: 10.1007/s00464-005-0867-1.
Takeshita K, Maruyama T, Murakami M, et al. Correction of scoliosis using segmental pedicle screw instrumentation versus hybrid constructs with hooks and screws. Stud Health Technol Inform 2006; 123:571-576.
Veldhuizen, A.G. et al., "A scoliosis correction device based on memory metal," Med. Eng. Phys., vol. 19 (2):171-179 (1997).
Wang A, Peng ), Zhang X, et al.Experimental study of recovery force of surface-modified TiNi memory alloy rod Sheng Wu Yi Xue Gong Cheng Xue Za Zhi. 2006;23:774-7.
Wever et al., "Scoliosis correction with shape-memory metal: results of an experimental study"; .Eur Spine J.; Apr. 2002; 11(2):100-6. Epub Nov. 14, 2001.
Wu S, Liu X, Chan YI,et al.Nickel release behavior, cytocompatibility, and superelasticity of oxidized porous single-phase NiTLJ Biomed Mater Res A. 2007; 81 :948-55.
Yeung KW, Poon RW, Chu PK,et al.Surface mechanical properties, corrosion resistance, and cytocompatibility of nitrogen plasma-implanted nickel-titanium alloys: A comparative study with commonly used medical grade materials.) Biomed Mater Res A. 2007; 82:403-14.
Suk SI, Kim W), lee SM, Kim )H, Chung ER. Thoracic pedicle screw fixation in spinal deformities: are they really safe? Spine 2001;26:2049-57.
Zdeblick ' Anterior Spinal Fixation after Lumbar Corpectomy' A Study in Dogs, Journal of Bone and Joint Surgery, vol. 73-A, #4, Apr. 1991, p. 527-534.
Zindrick MR, Knight GW, Satori MJ, et al. Pedicle morphology of the immature thoracolumbar spine. Spine 2000;25:2726-35.
European Search Report for GB0521589 dated Aug. 28, 2006.
European Search Report for GB07250128.1 dated Apr. 25, 2007.
Denkhausa K, Salnikow B. Nickel essentiality, toxicity, carcinogenicity[J]. Critical Reviews Oncology/Hematology, 2002, 42: 352-56.
Lu, "Treatment of scoliosis with a shape-memory alloy rod"; Zhonghua Wai Ke Za Zhi; Mar. 1986; 24(3):129-32, 187.

* cited by examiner

SPINAL ROD SUPPORT KIT

BACKGROUND

The present invention relates to a spinal support rod kit for the treatment of spinal column shape deformations.

Support rods which are used to support a spinal column can be fastened to the patient's vertebrae by means of fastening devices such as for example by bone screws or hooks. The support rods can help to support the spine in a desired alignment, for example during fusion of vertebrae.

Support rods are deformed prior to fixation to a patient's vertebrae, and forces are then applied to the vertebrae as the rods attempt to recover elastically toward their original undeformed configuration. Deformation of the rods can involve application of bending stresses and of torsional stresses. When it is desired to apply forces to a patient's spinal column through torsional deformation of a support rod, it can be preferred that the support rod has a non-circular cross-section, especially a square cross-section, which can be fitted into a channel in a fixation device whose cross-section is such that twisting of the rod in the channel is inhibited.

Maintaining a torsional deformation in a support rod requires that the rod is received in appropriate fixation devices at spaced apart points along its length. When this is done by fitting the rod into a channel in a fixation device with an appropriate non-circular cross-section, it can be difficult to locate the fixation device appropriately having regard to the variation in the cross-section of the rod as presented to the channel and the available vertebral tissue to which the fixation device might be fitted. This difficulty can be particularly acute in the thoracic region.

SUMMARY

The present invention provides a spinal support rod kit which includes a first spinal support rod, and a second spinal support rod with a socket at one end in which the end of the first rod can be received in an end-to-end arrangement.

Accordingly, in one aspect, the invention provides a spinal support rod kit for the treatment of spinal column shape deformations, comprising:

a first spinal support rod having a first cross-section at least at one end thereof, and a second spinal support rod which has a socket which is permanently connected to the said second support rod at one end which is shaped so that the said end of the first support rod can be received in the socket, the second support rod including a mechanical locking component which can engage the said end of the first support rod when it is inserted into the socket, to prevent it from being withdrawn.

The spinal support rod kit of the invention has the advantage that the second support rod enables the support rod assembly to be aligned torsionally with a channel in a fixation device which is intended to engage a selected vertebra, accommodating torsional misalignment of the first support rod, especially when the cross-section of the first support rod at its end is different from the cross-section of the second support rod.

Preferably, the cross-section of the first spinal support rod at the said end thereof is non-circular, especially approximately square. However, the cross-section of the first spinal support rod at the said end thereof might be approximately circular.

Preferably, the cross-section of the second support rod is circular along at least part of its length. The second support rod can then be received in a channel in a fixation device in any torsional orientation, enabling a desired torsional deformation to be maintained along the first and second support rods to ensure that appropriate torsional forces are applied to the vertebrae to which they are connected to ensure the desired correction of deformities.

The second support rod can have a non-circular cross-section. For example, it might have at least one flat side. It can be preferred that the second support rod has a plurality of flat sides. The second support rod can then be fitted into a channel in a fixation device whose cross-section is such that twisting of the rod in the channel is inhibited. The second support rod might have a square cross-section. The first support rod might have a square cross-section. When the second support rod and the socket for the first support rod have the same cross-section, it can be preferred that they are offset about the axis of the rod. For example, when the rod and the socket are both square, it can be preferred for one to be offset by about 45°.

A first support rod which has a non-circular cross-section can have at least one flat face. Preferably, the first spinal support rod has a regular or irregular polygonal shaped cross-section. The cross-section can be a polygonal shape having at least four faces, including square or rectangular or trapezoidal (when the rod has four faces when viewed in cross-section), or with six or eight or more faces. A first support rod which has a generally rounded cross-section might have a flat face. Preferably, the first support rod has a generally square cross-section.

The second support rod and the socket can be formed as one piece by a technique such as casting or machining, or the socket can be fastened permanently to the second support rod, for example by a technique such as brazing or welding.

Preferably, at least one of the first and second support rods is capable of recoverable deformation towards an original undeformed configuration (from which the support rods have been deformed) such that the angle between the ends of a support rod changes through at least about 20°, more preferably at least about 25°, especially at least about 30°. Recoverable deformation is deformation that can be recovered substantially completely back to the undeformed configuration when applied stress is removed, or otherwise when allowed to recover (for example as a result of heating to allow a transformation to austenite phase). Accordingly, it can be preferred for the first support rod or the second support rod or each of the first and second support rods to be formed from a shape memory alloy.

The first and second support rods will preferably have solid cross-sections. A support rod can be hollow along at least part of its length. One or more of the support rods can be in the form of a plate.

The cross-sectional area of a support rod will often be approximately constant over at least most of its length, with the possibility that the cross-section might vary in at least one end region to facilitate connection directly or indirectly to a vertebra at the end or to an adjacent support rod. For example, the cross-sectional area of the support rod might be at least about 10 mm$^2$, preferably at least about 20 mm$^2$, more preferably at least about 30 mm$^2$, for example about 40 mm$^2$.

The first and second support rods can differ from one another by features which include one or more of material, physical properties (for example modulus, elastic limit, etc which might for example be introduced through different processing techniques), and dimensions.

One or more support rods can be formed from a shape memory alloy. Preferably, the first support rod is made from a shape memory alloy. The alloy can be treated so that it is implanted while in the martensite phase. The treatment of the alloy can be such that its $A_s$ and $A_f$ temperatures are between ambient temperature and body temperature (37° C.), so that the alloy is fully austenite phase at body temperature (for example by virtue of the $A_f$ temperature being about 32° C.). This allows the surgeon to make use of the thermally initiated shape recovery properties of the alloy, in which the support rod is implanted in the body in the martensite phase, which is stable at ambient temperature. On implantation, the support rod is exposed to body temperature which leads to the phase of the alloy transforming from martensite to austenite. The support rod will then tend towards a configuration from which it was transformed while in the martensite phase, applying corrective forces to a patient's vertebrae.

A support rod which is formed from a shape memory alloy can apply corrective forces by virtue of the enhanced elastic properties that are available from such materials. Shape memory alloys can exhibit enhanced elastic properties compared with materials which do not exhibit martensite-austenite transformations and it is these properties that the present invention is concerned with in particular. The nature of superelastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document.

Examples of shape memory alloys which might be used in the first and possibly other support rods in the kit of the invention include nickel-titanium based alloys, especially the binary alloy which contains 50.8% nickel. Suitable alloys include those which satisfy ASTM F2063-00. It will often be particularly preferred for both the first and second support rods to be formed from shape memory alloys, especially for each support rod to be formed from shape memory alloys. Other metals which might be used to form support rods which do not exhibit shape memory properties include titanium and alloys thereof, for example Ti6Al4V alloys such as satisfy ASTM F136-02a or ASTM F1472-02a or both.

Materials which exhibit shape memory properties, other than alloys, can be used. For example, polymeric materials can be used. Shape memory properties can be imparted to polymeric materials by forming them in a desired ultimate shape (for example by moulding), crosslinking the material, heating the material to a temperature at which it softens, deforming the material while soft and restraining the material in the deformed configuration while it cools. The material will tend to revert towards the initial "as formed" configuration when reheated. Examples of suitable polymeric materials which can be used in this way include oligomers, homopolymers, copolymers and polymer blends which include, as monomers, l-, d- or d/l-lactide (lactic acid), glycolide (glycolic acid), ethers, ethylene, propylene and other olefins, styrene, norbornene, butadiene, poly-functional monomers such as acrylates, methacrylates, methyl acrylates, and esters such as caprolactone. The use of such polymeric materials in related applications is disclosed in WO-02/34310.

Preferably, the surface of the second spinal support rod has at least one spline. The at least one spline should preferably be located so that it is on the surface of the second support rod which is directed into the channel in a fixation device. The engagement of one or more splines on the second rod with corresponding splines in the channel in a fixation device can help to inhibit rotation of the second rod in the channel due to torsional stresses in the first support rod or the second support rod or both.

It will generally be preferred for each spline on the second support rod to extend approximately along the axis of the rod.

The spinal support rod kit will generally include a fixation device having a channel in which a support rod can be received, having a bone connection feature by which the device can be fastened to a patient's vertebra. The fixation device can be a bone screw, in which the channel is provided in or is otherwise fastened to the head of the screw, with a threaded shank extending from the head which can be screwed into a bore in the patient's bone tissue. The fixation device can be a hook which can be fitted on to a protrusion or recess in the patient's bone. The bone connection feature preferably extends below the lower surface of the support rods. Fixation devices having bone connection features of this general type (such as screws and hooks) for fastening spinal support rods to a patient's spinal column are known.

The fixation device can cooperate with a locking screw to retain a support rod in its channel. For example, the internal walls of the channel can have a circular cross-section when the channel is viewed along the axis of insertion of the support rod, and be threaded to engage a screw having a threaded peripheral surface, which is inserted into the channel. Alternatively or in addition, the external walls of the channel can have a circular cross-section when the channel is viewed along the axis of insertion of the support rod, and be threaded to engage a locking ring having a threaded internal surface, which can be positioned on the device so that the threads on the internal surface of the ring engage the corresponding threads on the external walls of the channel.

The fixation device can comprise a bone screw. The screw should be designed with an appropriate thread having regard to the nature of the tissue into which it is to extend. The factors affecting the suitability of a thread to engage bone tissue of a vertebra are well known, including thread pitch, shank diameter, thread diameter and so on.

The second support rod can have a fixation device by which the rod can be fastened to a patient's vertebra. The fixation device can be connected to the socket of the second spinal support rod, especially in such a way that the fixation device cannot be separate from the socket during or after implantation. For example, the socket can have a through hole extending through it to receive a bone screw. Alternatively, the socket can have a hook extending from its bone facing surface.

It can be preferred that the opening in the through hole to the inside of the socket is rounded when viewed from one side, and that the face of the head of the bone screw which faces towards the lower surface of the socket can have a correspondingly rounded shape. This can enable the bone screw to be screwed into bone tissue with the angle between the axis of the screw and the axis of the through hole being greater than 0°, for example at least about 5°, or at least about 10°, or possibly at least about 15°.

The socket provided by the second spinal support rod can have a closed cross-section at its open end when viewed along the longitudinal axis of the rod. The end of the first support rod can be inserted through the open end into the socket of the second support rod in a direction along the longitudinal axis of the second spinal support rod. In order to connect the first and second support rods, there must be sufficient space in the direction of the longitudinal axes of the rods between the end of the first support rod and the socket of the second support rod.

Alternatively, the socket can have an open cross-section at its open end when viewed along the longitudinal axis of the second spinal support rod. The end of the first spinal support rod can be inserted into the socket of the second spinal support rod by moving the end of the first support rod relative to the socket of the second support rod in a direction which is generally transverse to the longitudinal axis of the second support rod. This socket has the advantage that the amount of space required to connect the first and second support rods, when measured in a direction along the longitudinal axis of the rods, is reduced. Prior to the connection of the first and second support rods, the end of the first support rod can overlap with the socket at the end of the second support rod. This reduces the space required by the surgeon to connect the spinal support rods.

The socket can be shaped and dimensioned to receive the correspondingly shaped end of the first spinal support rod. The end of the first support rod preferably forms a tight sliding fit with the socket.

The outer surface of the wall of the socket can also include one or more engagement members, such as for example a groove, a recess or a protrusion which can cooperatively engage corresponding engagement members, such as for example a ridge, a protrusion or a recess on surgical instruments, such as for example a rod approximator instrument. This has the advantage that the surgeon can use a surgical instrument to locate the socket to help connect or disconnect the end of the first support rod to or from the socket of the second support rod.

The locking component of the second support rod preferably comprises a threaded fastener, which can engage a surface of the socket so that it can be driven towards the surface of the first support rod when received in the socket. It will generally be preferred for the internal wall of the socket to be threaded and for the fastener to have a threaded peripheral surface.

Preferably, the kit of the invention includes a transverse arm which can extend from one of the first and second spinal support rods generally transversely to a patient's spinal column. Preferably, the transverse arm is provided as a separate component and the kit can then include a connector by which the transverse arm can be connected to one of the first and second support rods.

A transverse arm which is fastened to the second support rod can help to inhibit rotation of the second rod due to torsional stresses in the first support rod or the second support rod or both. The connection between the second support rod and a transverse arm should preferably be capable of preventing relative movement (for example involving rotation of the second support rod about its axis relative to the transverse arm) due to torsional stresses in the second support rod.

The transverse arm can be fastened to the patient's vertebra at its end which is remote frm the first and second support rods. Preferably, the kit includes a third spinal support rod for fixation to a patient's spinal column approximately parallel to the first and second support rods, and a connector by which the said transverse arm can be connected to the third support rod. The kit can include appropriate fixation devices by which the third support rod can be fixed to the patient's vertebrae.

It can be preferred for the transverse arm to have at least one longitudinally extending spline which extends along at least part of its length. This spline can cooperate with a cooperating spline on the first or second support rod. This spline helps to secure the arm and can prevent the transverse arm from twisting about its axis. This spline can therefore increase the torsional stability of the system.

The cross-sectional area of the transverse arm will often be approximately constant over at least most of its length, with the possibility that the cross-section might vary in at least one end region to facilitate connection directly or indirectly to a vertebra or to the first or second spinal support rods. For example, the cross-sectional area of the transverse arm might be at least about 10 mm$^2$, preferably at least about 20 mm$^2$, more preferably at least about 30 mm$^2$, for example about 40 mm$^2$.

The length of the transverse arm can be selected according to the requirements of a particular application. It is expected that it will seldom be required to be longer than about 50 mm. The length of the transverse arm will usually be at least about 15 mm.

The support rods, the transverse arm and the fixation devices can be made from one or more metallic materials as is generally known for components of spinal implant kits. Suitable metals include certain stainless steels, and titanium and its alloys. It can be preferred that the transverse arm at least is formed from a material which enables the arm to be cut to length to suit a particular application.

BRIEF DESCRIPTION OF THE DRAWINGS

Embodiments of the invention will now be described by way of example with reference to the accompanying drawings, in which.

DETAILED DESCRIPTION

In general, the present invention provides a spinal support rod kit comprising first and second support rods for the treatment of spinal column shape deformations.

Figure 1:
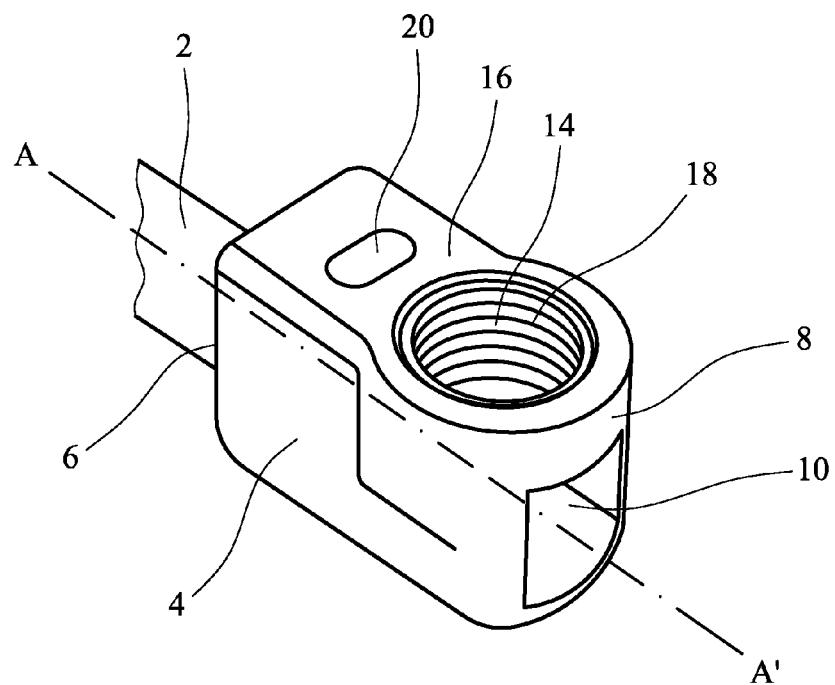
FIG. 1 is a perspective view of the socket of the second support rod of one embodiment of the present invention.
Figure 2:
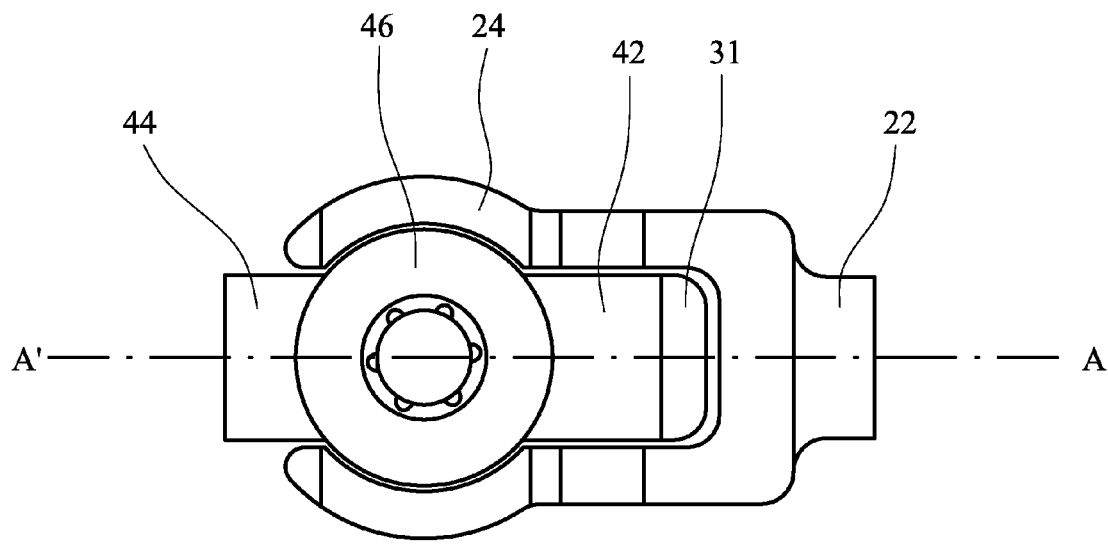
FIG. 2 is a view from above of the socket of the second support rod of a further embodiment of the present invention connected to an end of the first support rod.
Figure 3:
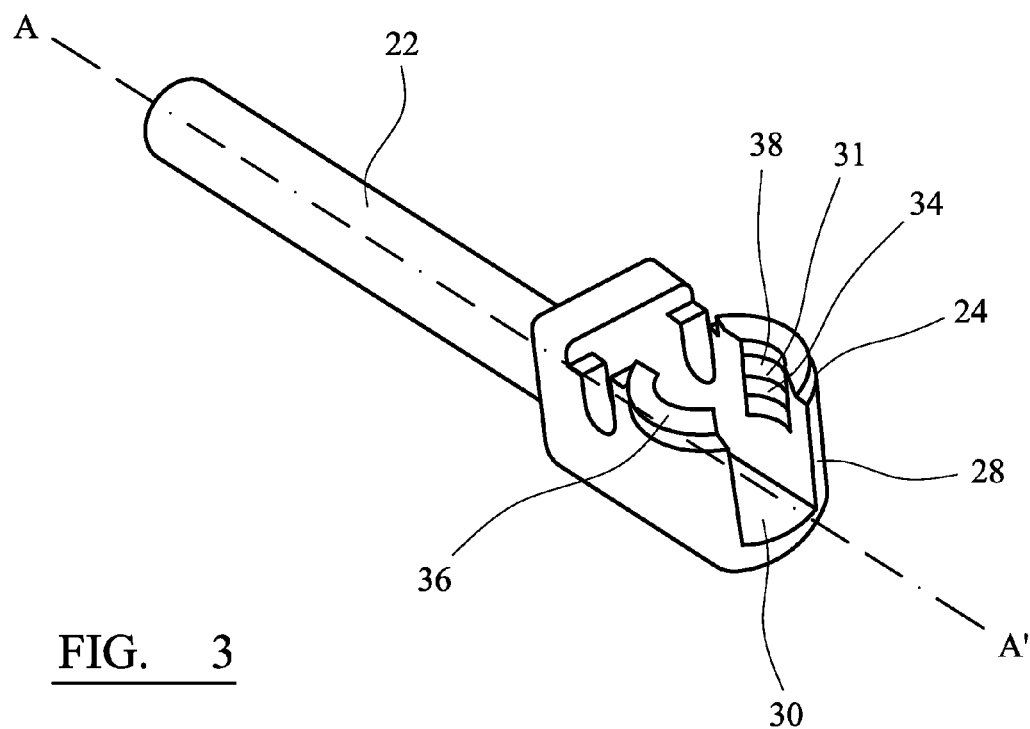
FIG. 3 is a perspective view of the second support rod of the embodiment of FIG. 2.
Figure 4:
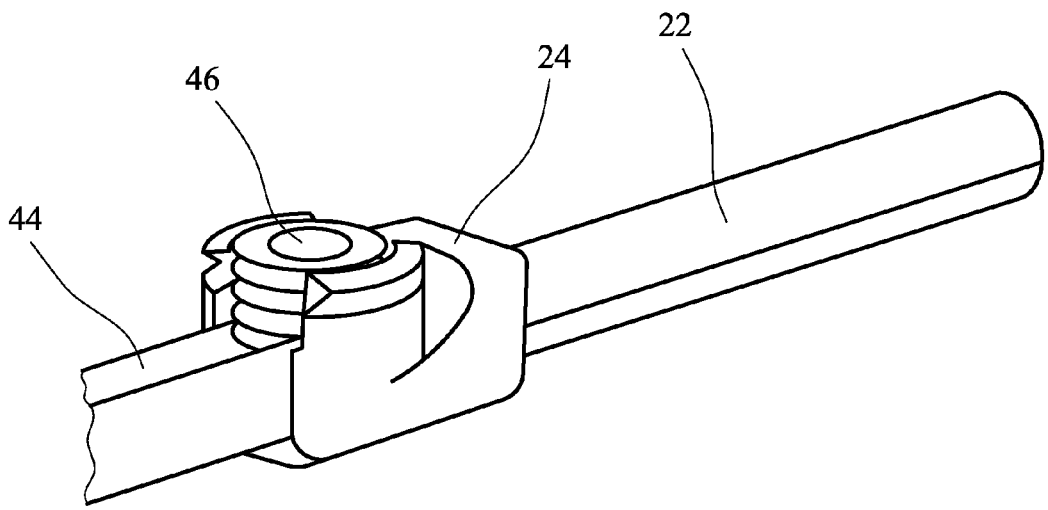
FIG. 4 is a perspective view of the first and second support rods of the embodiment of FIG. 2.
Figure 5:
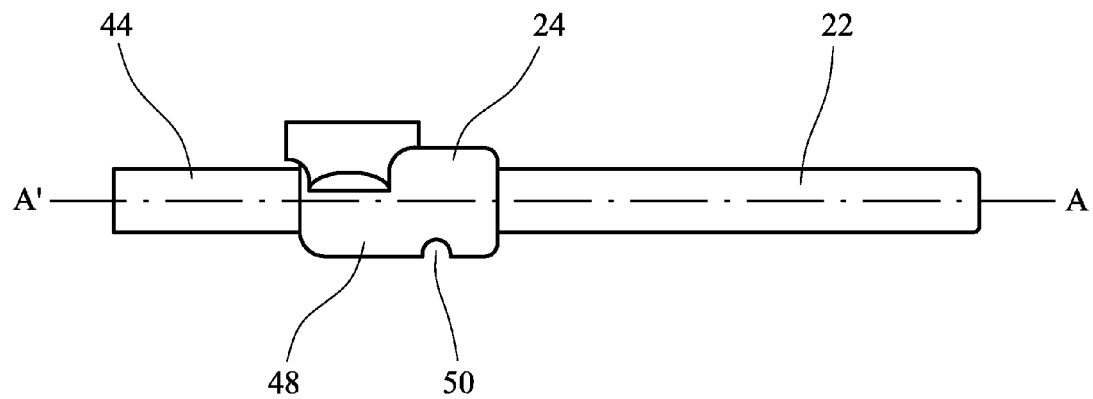
FIG. 5 is a side view of the first and second support rods of the embodiment of FIG. 2.

With reference to FIG. 1, the second spinal support rod 2 is composed of stainless steel and has a circular cross-section. The second support rod 2 has a solid cross-section. The cross-sectional area of the second support rod 2 is approximately constant over the entire length of the second support rod 2.

A socket 4 is permanently connected to one end 6 of the second support rod 2. The socket 4 has a closed cross-section at its open end 8 when viewed along the longitudinal axis A-A' of the second support rod 2. The open end 8 provides an opening 10 having a square shape which is dimensioned to receive an end of a first spinal support rod (not shown) which has a square cross-section. The opening 10 is in communication with a channel (not shown) which extends in the direction of the longitudinal axis A-A' of the second support rod 2.

The upper surface 16 of the socket 4 provides an aperture 14. The aperture 14 is in communication with a threaded bore 18 which extends substantially perpendicular to the longitudinal axis A-A' of the second support rod 2. The threaded bore 18 also extends substantially perpendicular to the channel (not shown) which is in communication with the opening 10. The upper surface 16 of the socket 4 also provides an opening 20 which is dimensioned to receive an end of a surgical tool (not shown) for locating the socket 4.

In use, the surgeon uses a surgical tool to locate the opening 20 provided by the socket 4 of the second support rod 2. An end of a first spinal support rod (not shown) having a square cross-section is inserted through the opening 10 in the open end 8 of the socket 4 of the second support rod 2. The first support rod (not shown) is inserted into the socket 4 in the direction of the longitudinal axis A-A' of the second support rod 2.

A locking component (not shown) of the second support rod 2 is inserted into the aperture 14 provided by the upper surface 16 of the socket 4. The locking component (not shown) comprises a threaded screw (not shown) which cooperatively threadingly engages the threaded bore 18 provided by the socket 4 of the second support rod 2. The threaded screw (not shown) engages the end of the first support rod (not shown) and prevents the first support rod (not shown) from being withdrawn from the socket 4 of the second support rod 2.

Once the end of the first support rod (not shown) is secured within the socket 4 of the second support rod 2 torsional stability is maintained along the first and second support rods 2 of the invention. The second support rod 2 is not able to rotate relative to the first support rod (not shown).

With reference to FIGS. 2 to 5 and 7, the socket 24 of the second support rod 22 has an open configuration provided by a rectangular opening 30 at its open end 28 when viewed along the longitudinal axis A-A' of the second support rod 22. The rectangular opening 30 in the open end 28 is in communication with a channel 31 which extends in the direction of the longitudinal axis A-A' of the second support rod 22. The opening 30 and the channel 31 of the second support rod 22 are dimensioned to receive an end 42 of the first support rod 44.

The end 42 of the first support rod 44 has a square cross-section. The rectangular opening 30 provided at the open end 28 of the second support rod 22 has a width which is slightly greater than the width of the end 42 of the first support rod 44.

The socket 24 provides an aperture 34 in the upper surface 36 of the socket. The aperture 34 is in communication with a threaded bore 38 which extends substantially perpendicular to the longitudinal axis A-A' of the second support rod 22. The threaded bore 38 also extends substantially perpendicular to the longitudinal axis of channel 31. Prior to connection of the first 44 and second 22 rods, the end 42 of the first support rod 44 overlaps with the socket 4 of the second support rod 22.

The second support rod 22 comprises a locking component 46 which is dimensioned to be inserted through the aperture 34 provided by the socket 24. The locking component 46 comprises a threaded screw.

The lower surface 48 of the support rod 22 has a spline 50. The spline 50 extends along the lower surface 48 of the socket 24 in a direction which is substantially perpendicular to the longitudinal axis A-A' of the second support rod 22.

In use, the square end 42 of the first support rod 44 is inserted through the opening 30 into the channel 31 of the socket 24 by moving the end 42 of the first support rod 44 relative to the socket 24 of the second support rod 22. The end 42 of the first support rod 44 is moved in a direction which is generally transverse to the longitudinal axis A-A' of the second support rod 22.

A locking component 46 of the second support rod 22 is inserted through the aperture 34 into the channel 31 of the socket 24. The locking component 46 cooperatively threadingly engages the threaded bore 38 provided by the socket 24 of the second support rod 22. The threaded screw 46 engages the end 42 of the first support rod 44 and prevents the first support rod 44 from being withdrawn from the socket 24 of the second support rod 22.

Once the end 42 of the first support rod 44 is secured within the socket 24 of the second support rod 22 torsional stability is maintained along the first 44 and second support rods 22 of the invention. The second support rod 22 is not able to rotate relative to the first support rod 44.

Figure 6:
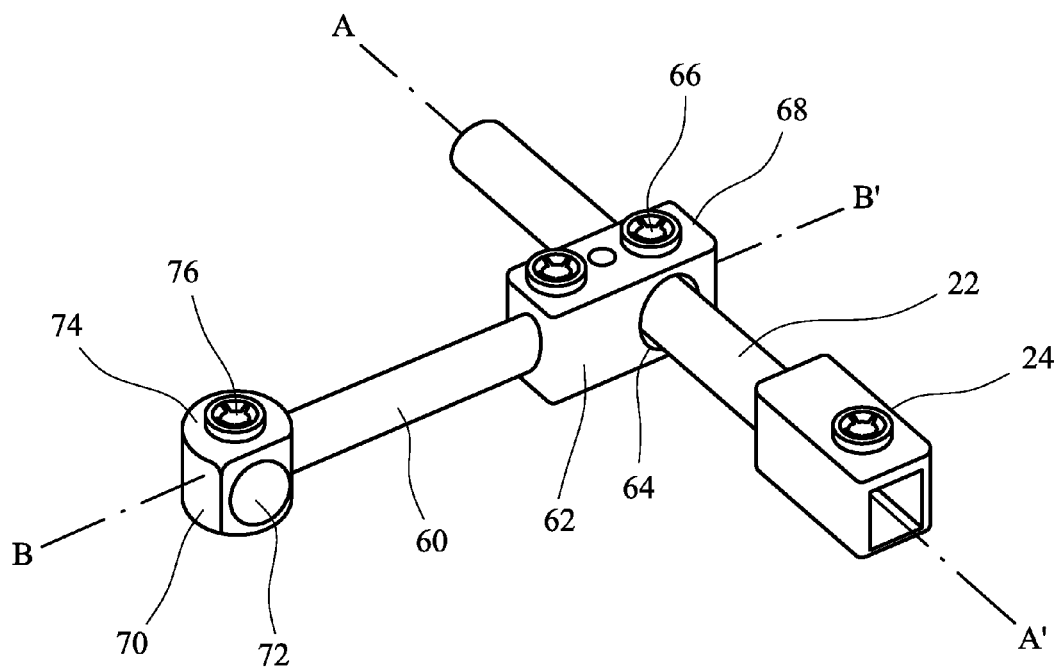
FIG. 6 is a perspective view of the transverse arm and the second support rod of the embodiment of FIG. 1.
Figure 7:
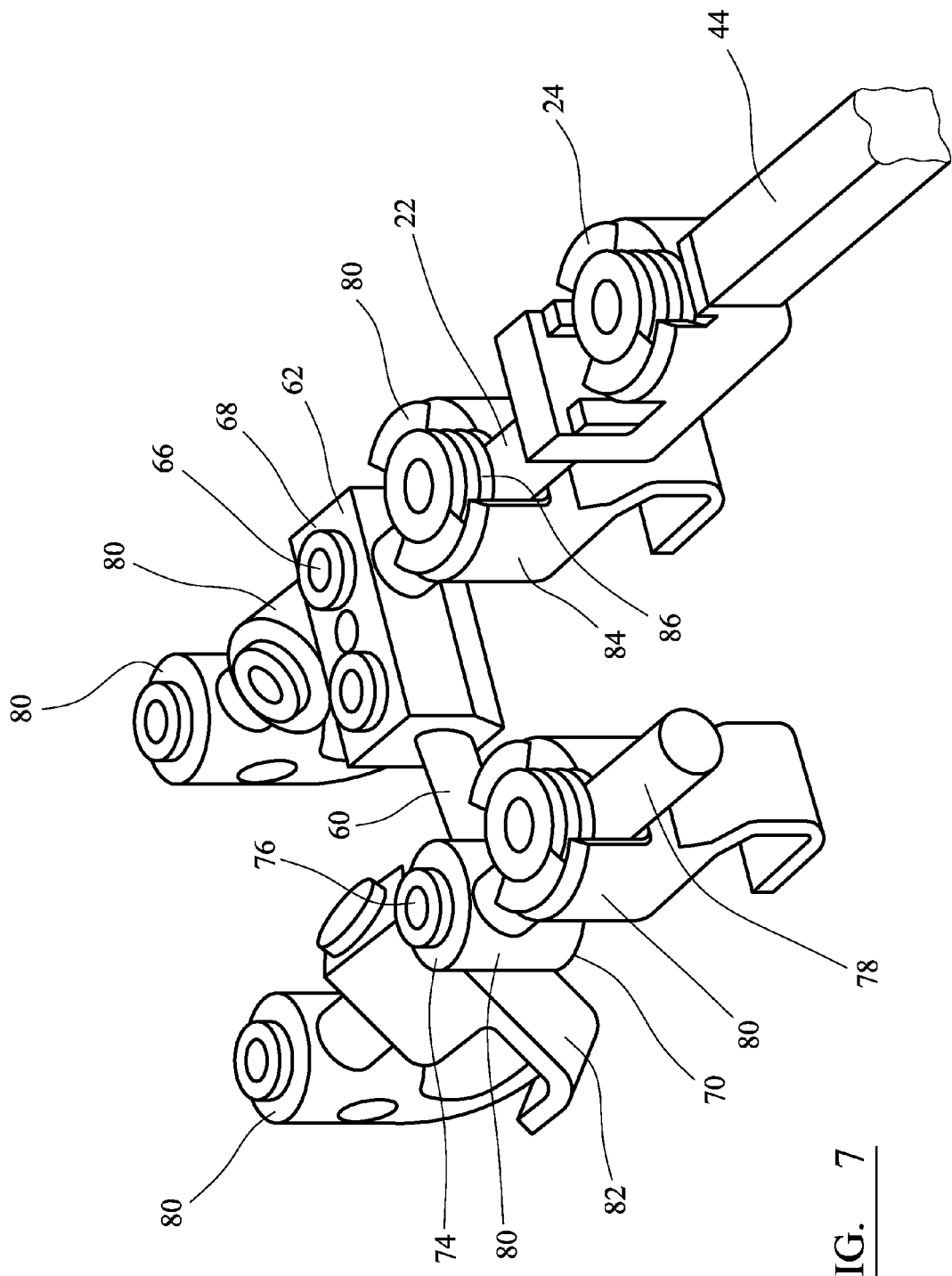
FIG. 7 is a perspective view of the assembled kit of the embodiment of FIG. 2.

With reference to FIGS. 6 and 7, the second support rod 2 and 22 can be connected to a transverse arm 60. The transverse arm 60 extends from the second support rod 2 and 22 substantially perpendicular to the longitudinal axis A-A'. The transverse arm 60 and the second support rod 2 and 22 are provided in the kit as separate parts. The transverse arm 60 includes a connector 62 which is permanently connected to one end of the arm 60. The connector 62 has a through hole 64 extending substantially perpendicular to the longitudinal axis B-B' of the transverse arm 60. The through hole 64 has a circular cross-section. The through hole 64 is dimensioned to receive the second support rod 2 and 22. The diameter of the through hole 64 is slightly greater than the diameter of the second support rod 2 and 22.

A threaded bore 66 extends from the upper surface 68 of the connector 62. The threaded bore 66 extends substantially perpendicular to the longitudinal axis B-B' of the transverse arm 60. The threaded bore 66 also extends substantially perpendicular to the longitudinal axis of the through hole 64.

The end 70 of the transverse arm 60 which is remote from the connector 62 of the transverse arm 60 also provides a through hole 72. The through hole 72 has a circular cross-section. Through hole 72 extends substantially perpendicular to the longitudinal axis B-B' of the transverse arm 60. The longitudinal axis of through hole 72 is substantially parallel to the longitudinal axis of through hole 64.

The upper surface 74 of the end 70 of the transverse arm 60 provides an aperture 76. The aperture 76 is in communication with a threaded bore (not shown). The threaded bore (not shown) in the end 70 extends substantially perpendicular to both the longitudinal axis of the through hole 72 and the longitudinal axis B-B' of the transverse arm 60. The threaded bore (not shown) extends in a direction substantially parallel to the threaded bore 66 of the connector 62.

In use, the second support rod 2 and 22 is inserted into the through hole 64 of the connector 62 of the transverse arm 60. The longitudinal axis A-A' of the second support rod 2 and 22 extends substantially perpendicular to the longitudinal axis B-B' of the transverse arm 60. A threaded screw (not shown) is inserted into the threaded bore 66 of the connector 62. The threaded screw cooperatively engages the threaded bore 66 and the second support rod 2 and 22 is secured within the through hole 64 of the connector 62.

A third rod 78 having a circular cross-section is inserted through the through hole 72 at the end 70 of the transverse arm 60. The diameter of the through hole 72 is slightly greater than the diameter of the third rod 78. A threaded screw (not shown) is inserted into the threaded bore 76. The threaded screw (not shown) cooperatively engages the threaded bore 76 and the third rod 78 is secured within the through hole 72 of the transverse arm 60. The third rod 78 extends substantially parallel to the first 44 and second 2 and 22 rods.

With reference to FIG. 7, the kit includes six fixation devices 80. Each fixation device 80 comprises a hook 82 and a housing 84. The housing 84 comprises a channel (not shown) which is adapted to receive a support rod having a circular cross-section. The inner surface of the housing 84 also provides a threaded bore (not shown).

In use, the second 2 and 22 and third 78 rods are inserted through the channel (not shown) of a fixation device 80. The hook 82 extends below the plane of the lower surface 48 of the socket 4 and 24 and the rods 2, 22 and 78. A threaded screw 86 is inserted into the threaded bore (not shown) of each fixation device 80 to engage the support rod 2, 22 or 78. The assembled kit includes three fixation devices 80 which are engaged to the second support rod 2 and 22. Three fixation devices 80 are engaged to the third rod 78. The fixation devices 80 which are engaged to the second support rod 2 and 22 are spaced apart from the fixation devices 80 which are engaged to the third rod 78 by the transverse arm 60. The spacing is sufficient so that three fixation devices 80 can be connected to each side of the spine in a claw formation.

What is claimed is:

1. A spinal support rod kit for the treatment of spinal column shape deformations, comprising:
   a first bone anchor for connecting to a first vertebra;
   a second bone anchor for connecting to a second vertebra;
   a third bone anchor for connecting to a third vertebra;
   a first spinal support rod connectable to the first bone anchor and the second bone anchor to fix the first vertebra to the second vertebra, the first spinal support rod having a first end, a second end, and a length spanning from the first end to the second end, the cross section having two opposed flat sides connected by a top surface, the rod terminating at the first end with a first planar end surface intersected by and oriented perpendicular to the flat sides, the rod terminating at the second end with a second planar end surface intersected by and oriented perpendicular to the flat sides, the first spinal support rod having a uniform cross-section along an entirety of the length of the rod from the first planar end surface to the second planar end surface, the first spinal support rod being formed from a shape memory alloy having thermally initiated shape recovery properties, wherein the first spinal rod is operable to apply corrective forces to the vertebra through the first and second bone anchors by the thermally initiated shape recovery properties of the shape memory alloy,
   a second spinal support rod connectable to the third bone anchor, the second spinal rod having a socket which is permanently connected to the second support rod at one end, the socket receiving the first end of the first spinal support rod, the socket having opposed side walls, the side walls each being generally flat in shape and including a portion of an internal thread, and
   a set screw engageable with the internal thread of the socket to prevent the first spinal support rod from being withdrawn from the socket, whereby the first spinal support rod is connected to the second spinal support rod to fix the first, second and third vertebra relative to each other.

2. The spinal support rod kit of claim 1, in which the cross-section of the second support rod is circular along at least part of its length.

3. The spinal support rod kit of claim 1, in which the surface of the second support rod is splined along at least part of its length.

4. The spinal support rod kit of claim 1, in which the socket has a closed cross-section at its open end when viewed along the longitudinal axis of the second support rod.

5. The spinal support rod kit of claim 1, in which the socket has an open cross section at its open end when viewed along the longitudinal axis of the second support rod, allowing the end of the first support rod to be located in the socket by movement in a direction which is generally transverse to the axis of the second support rod.

6. The spinal support kit of claim 1, in which the second support rod is formed from a shape memory alloy.

7. The spinal support kit of claim 1, in which the cross section of the first spinal support rod is approximately square.

* * * * *